United States Patent [19]
Levin

[11] Patent Number: 6,167,298
[45] Date of Patent: Dec. 26, 2000

[54] DEVICES AND METHODS FOR MAINTAINING AN ALERT STATE OF CONSCIOUSNESS THROUGH BRAIN WAVE MONITORING

[76] Inventor: Richard B. Levin, 375 Walnut Ave., Apt. E, Carlsbad, Calif. 92008

[21] Appl. No.: 09/227,802

[22] Filed: Jan. 8, 1999

Related U.S. Application Data

[60] Provisional application No. 60/070,847, Jan. 8, 1998.

[51] Int. Cl.[7] ....................................................... A61B 5/04
[52] U.S. Cl. .............................................................. 600/545
[58] Field of Search ..................................... 600/545, 544

[56] References Cited

U.S. PATENT DOCUMENTS

| | | | |
|---|---|---|---|
| 5,295,491 | 3/1994 | Gevins | 600/545 |
| 5,311,877 | 5/1994 | Kishi | 600/545 |
| 5,377,100 | 12/1994 | Pope et al. | 600/545 |
| 5,601,090 | 2/1997 | Musha | 600/545 |
| 5,626,145 | 5/1997 | Clapp et al. | 600/545 |
| 5,788,648 | 8/1998 | Nadel | 600/545 |
| 5,813,993 | 9/1998 | Kaplan et al. | 600/545 |

*Primary Examiner*—Cary O'Connor
*Assistant Examiner*—Navin Natnithithadha
*Attorney, Agent, or Firm*—Calif Tervo

[57] ABSTRACT

Disclosed are devices for monitoring and maintaining an alert state of consciousness in a subject wearing the device. An alert mental state is maintained through monitoring of brain wave patterns to detect if a transition from an alert to a non-alert mental state is about to occur, or has occurred. If so, a stimulus, e.g., an audible tone, is provided until such time as an alert mental state, as assessed by brain wave activity, is restored. Also disclosed are methods for maintaining an alert mental state, as well applications for such devices and methods.

22 Claims, 1 Drawing Sheet

DEVICES AND METHODS FOR MAINTAINING AN ALERT STATE OF CONSCIOUSNESS THROUGH BRAIN WAVE MONITORING

This application claims the benefit of U.S. Provisional Ser. No. 60/070,847 filed Jan. 8, 1998.

TECHNICAL FIELD OF THE INVENTION

The invention relates to devices and methods for maintaining an alert state of consciousness. In particular, this invention relates to devices and methods for monitoring brain waves to detect patterns associated with a non-alert state of consciousness, in which event a stimulus is then provided to restore an alert mental state.

BACKGROUND OF THE INVENTION

Maintenance of an alert mental state of consciousness is important in many fields for many reasons. For example, the American Medical Association's Council on Scientific Affairs published a report indicating that driver drowsiness and fatigue are involved in at least about 1.5% of the nation's annual 6.3 million vehicle accidents. Of those accidents involving drowsiness, about 96% involved passenger vehicles; the remainder involved trucks. In addition to the transportation industry, many other fields incur substantial revenue and productivity losses due to individuals unintentionally transitioning from an alert state of consciousness to a non-alert state. Avoiding or delaying such transitions would have enormous economic and societal benefit.

Prior to this invention, no device existed which could prevent or delay the onset of an unintentional transition from an alert mental state to a non-alert state of consciousness through the monitoring of brain wave patterns. Instead, in order to prevent such transitions, various other approaches have been applied. For example, chemical stimulants have long been used in order to maintain an alert state of consciousness for a period longer than would be experienced absent the stimulant. Alternatively, in some fields time periods during which a particular function requiring that an alert state of consciousness be maintained have been established in order to ensure the desired level of consciousness is maintained throughout.

More recently, several devices have been developed which monitor and respond to physical manifestations of fatigue or drowsiness. For example, U.S. Pat. No. 5,402,109 describes an eyeglass-attachable alarm signal device designed to prevent automobile and truck drivers from falling asleep while driving. The device employs a small slide-adjustable light emitter which produces a beam of a narrow-band light to optically sense whether the driver's eyelids are opened or closed. The light beam is aimed across the surface of the driver's eye, just above the eyeball, between the eyelids, and it is sensed in the opposite corner of the eye by a light sensor. When the device detects that a driver's eyes have been closed for longer than a predetermined time, e.g., about one second, an electronic circuit activates an alarm.

Another device to monitor and restore alertness is described in U.S. Pat. No. 5,626,145. Specifically, that device automatically detects alertness in a subject by collecting brain wave data from a subject using an electroencephalogram or magnetoencephalogram. The brain wave data is then separated from other data, e.g., data resulting from eye blinks, chewing, and other movements not related to brain activity, using a zero phase quadratic filter. The non-brain wave data is then further analyzed to detect alertness. Thus, these devices do not monitor states of consciousness by analysis of brain waves or brain wave patterns, but instead rely on physical manifestations of states of consciousness.

In contrast, it is the object of this invention to provide devices which allow an alert state of consciousness to be maintained through the use of a device which monitors and interprets brain wave patterns of an individual wearing the device. When the device detects in the wearer a brain wave pattern associated with a non-alert state of consciousness, a transient physical stimulus is then provided to restore the desired mental state.

SUMMARY OF THE INVENTION

One aspect of the invention concerns devices for maintaining a state of mental alertness. Generally, such devices include, but are not limited to, one or more brain wave sensors used to monitor one or more brain wave types in a subject in whom an alert mental state is to be maintained, a processor capable of analyzing brain wave patterns detected by the brain wave sensor(s) to determine if the subject is in an alert mental state, an alarm component for delivering a stimulus to capable of restoring an alert mental state, and a power supply.

In preferred embodiments of this aspect of the invention, the brain wave sensors used in the device comprise electrodes that make contact with skin of the subject's, or user's, head. In such embodiments, the electrode(s) is(are) configured to detect the desired brain wave(s) to be analyzed. If necessary, the sensor (or processor) also includes elements, e.g., circuitry, required for the sensor (e.g., an electrode) to produce a signal (e.g., a digital signal) that can be input into an analyzed by the processor. In those embodiments where the sensor is not operably connected to the processor, for example, the sensor(s) detects brain waves, and this information is transmitted to a remotely positioned processor integrated with an appropriate receiver, etc.

In these and other embodiments of this aspect of the invention, the brain wave sensor(s) used in the device can detect at least one brain wave type, or form (e.g., alpha, beta, delta, or theta brain waves), and preferably can detect a plurality of, and preferably all brain wave forms, including such forms as alpha spindles and theta bursts.

In preferred embodiments of the device according to the invention, the processor is operably associated with (e.g., functionally connected to) the brain wave sensor(s) employed, and is capable of being worn by the user wearing the brain wave sensor(s). Preferably, the brain wave pattern (s) and/or wave(s) detected by the brain wave sensor(s) are input into the processor and analyzed. Typically, brain wave data (i.e., data concerning one or more brain wave forms or and/or patterns) is analyzed by comparing the detected brain wave(s) and/or brain wave pattern(s) against a library of brain wave(s) and/or pattern(s) (typically stored in a memory operably connected to the processor) in order to determine if a brain wave form and/or pattern input into the processor is indicative of a non-alert mental state. In particularly preferred embodiments, the library of brain wave(s) and/or pattern(s) is derived previously from the same subject while in an alert state of consciousness. Alternatively, the library may be based on data gathered from a plurality of test subjects during the course of vigilance testing, or other testing designed to produce detectable performance decrements, particularly a non-alert mental state, during the course of the test.

In preferred embodiments of this aspect of the invention, the processor analyses digital signals derived from the brain wave data detected by the brain wave sensor(s). Preferably, the subject's brain wave activity is analyzed at least once every fifteen seconds, with monitoring and analysis of the subject's brain waves and/or patterns at least once per second being particularly preferred. Especially preferred periods for frequencies of analysis are once per 0.1, 0.05, 0.01, or 0.001 second. Of course, continuous monitoring may also be performed, particularly when the period of time the user uses the device is of short duration, or when power requirements are not a concern, for example, when power for the device is supplied from a source such as a vehicle's electrical system.

In particularly preferred embodiments, the processor can also calculate one or more brain wave ratios, wherein the amount of a particular brain wave type over a given time unit is compared to the amount of another brain wave type over an equal, particularly the same, time period. Such calculations are well known in the art, e.g., integration. In such embodiments, it is useful to detect not only the period over which one or more brain wave types occurs, but also the amplitude(s) of such activity during that period. When a ratio, or that correlates with a non-alert state is detected, or preferably, when several such ratios are determined within a given period, the processor may then perform a routine to generate a stimulus to restore an alert mental state. Particularly preferred ratios include an alpha:beta ratio. What constitutes a ratio that correlates with a non-alert mental state can vary, particularly from person to person, as those in the art will appreciate. For this reason, the ratio(s) used for a particular user are preferably determined in advance, for example, by vigilance testing, where observable decrements in performance of one or more tasks are correlated with brain wave activity. When the performance level of the task(s) being performed declines below a particular level, for example, below about 75%, preferably below about 80%, more preferably below about 85%, even more preferably below about 90%, especially more than below about 95% of maximum performance, the brain wave(s) and/or patterns then detected are determined to correlate with a non-alert mental state. As those in the art will appreciate, what constitutes a non-alert mental state may vary depending upon the task (e.g., driving, listening, operating dangerous machine tools, etc.) for which a minimum desired level of consciousness is required.

In yet other preferred embodiments of this aspect of the invention, upon detection of a non-alert state, the device's alarm component is actuated to emit a stimulus, or series of stimuli, perceptible to the user in a manner sufficient to transition the subject from a non-alert mental state to an alert mental state. In certain of these embodiments, the stimulus emitted from or produced by the alarm component is selected from the group consisting of an auditory stimulus, a visual stimulus, an electrical stimulus, a vibratory stimulus, and a combination of more than one of the foregoing stimuli. In particularly preferred embodiments employing an auditory stimulus, the alarm component of the device is positioned in or adjacent to an ear canal of the user in a manner such that when the stimulus is emitted, it can be perceived by the user and restores an alert mental state in the user. Particularly preferred are devices wherein the auditory stimulus, or one or more other stimuli, can be selected by the user wearing the device.

In other preferred embodiments, the device's power supply comprises one or more batteries.

Preferably a device according to the invention comprises one or more brain wave sensors integrated into a headband that can be worn by the user. Preferably, the device also includes an alarm and processor such that when the components are integrated they comprise a single removable apparatus that can be worn comfortably on a user's head. Even more preferred are such devices that further comprise a power supply. Other components, e.g., a transmitter, receiver, other physiological monitoring devices, etc., can also be incorporated into a device according to the invention.

Another aspect of this invention concerns methods for monitoring an alert state of consciousness in a subject. Such methods typically comprise detecting one or more brain wave forms and/or patterns or ratios in the subject and correlating such wave form(s), pattern(s), and/or ratio(s) with an alert or non-alert state of consciousness.

Yet another aspect of this invention concerns methods for maintaining an alert state of consciousness through the use of a device according to the invention. Certain of these embodiments involve detecting a brain wave pattern in the subject and determining if the brain wave activity detected is indicative of an alert state of consciousness, and if not, stimulating the subject until brain activity indicative of an alert state of consciousness is detected. Yet other embodiments of this aspect concern determining if the subject is producing brain activity indicative of a non-alert state of consciousness and, if so, providing a stimulus, or series of stimuli, until an alert mental state is restored.

DETAILED DESCRIPTION OF THE INVENTION

Figure 1:
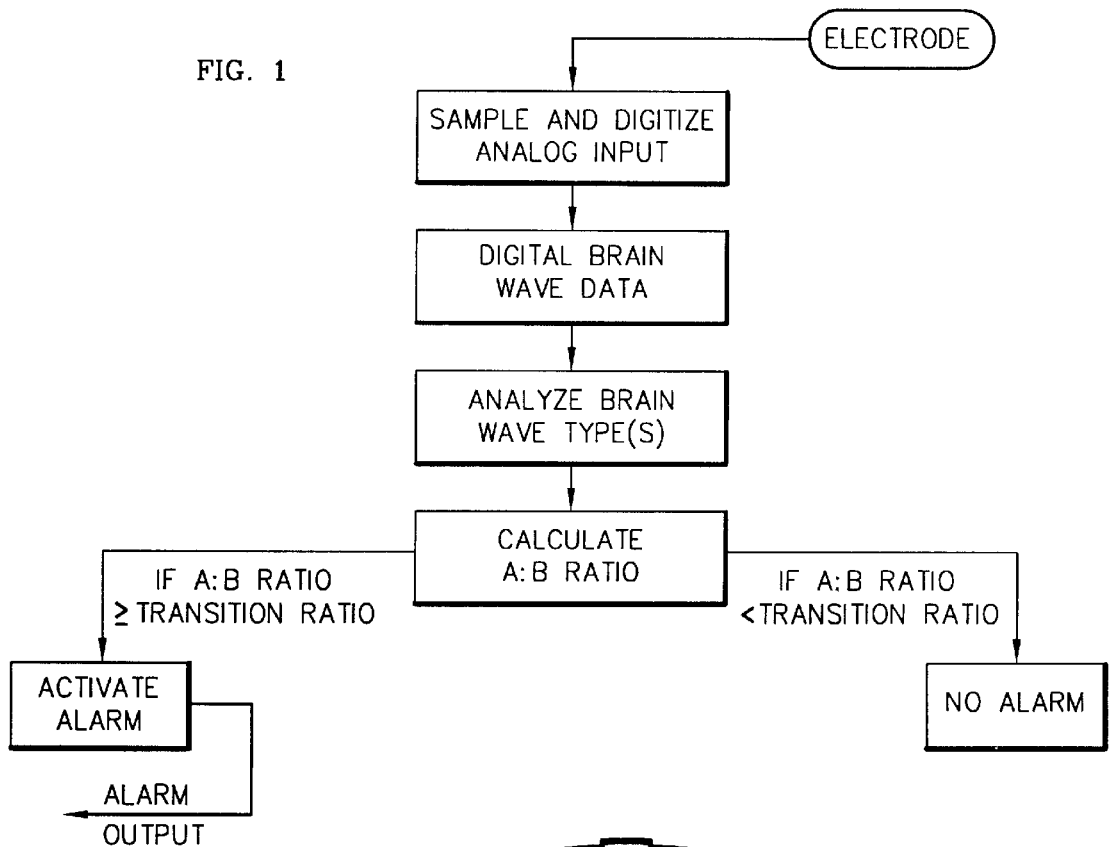
FIG. 1 is a block diagram of a representative algorithm useful in monitoring brain wave forms or patterns in analog form, analyzing whether the waves or patterns being monitored are indicative of an alert state of consciousness, and if not, instructing that a stimulus be administered to restore the desired state of consciousness.

The present invention is based on the development of a device capable of monitoring the brain wave patterns of a subject wearing the device in order to determine when the subject transitions from an alert mental state of consciousness to a non-alert mental state. Upon detection of a transition from an alert to a non-alert state of consciousness, the device delivers a physical stimulus to the subject to restore the desired state of consciousness, i.e., an alert mental state, to the subject.

As used herein, an "alert mental state" or "alert state of consciousness" shall refer to a mental state wherein the brain wave pattern of the subject is indicative of an alert mental state. Whether or not a subject is in an alert mental state can be determined by monitoring one or more brain waves, or brain wave patterns, alone or in combination with detecting physical manifestations of a non-alert mental state, e.g., eye blinks and jaw movement. In contrast, a "non-alert mental state" or "non-alert state of consciousness" shall be any mental state or level of consciousness other than an alert mental state.

A brain wave pattern associated with an alert mental state is that which occurs in a subject when the subject is alert. Such a pattern may be based on an average obtained by analysis of the brain wave patterns of at least two subjects in an alert mental state when the pattern is monitored. Alternatively, such a brain wave pattern may be specific to the particular subject, and is preferably established by averaging the results obtained by monitoring the brain wave patterns of the subject at least twice while in an alert mental state. Such patterns may be initially established by monitoring brain wave patterns at the same time as other parameters indicative of an alert or non-alert mental state are also monitored. For example, detection of physical manifestations of a mental state can be using the device described in U.S. Pat. No. 5,626,145. When one or more physical manifestations of a non-alert mental state are detected, a brain wave pattern then occurring, or, preferably, which immediately preceded the physical manifestation, is recorded and used to establish the pattern indicative of a non-alert mental state.

Alternatively, in a preferred embodiment of the invention, the brain wave pattern of a subject in an alert mental state and a non-alert mental state, and the transition from an alert to a non-alert mental state, are monitored while the subject performs a task the adequate performance of which requires an alert mental state. Such tasks may include manual dexterity testing, mathematical problem solving, reading comprehension tests, or any other vigilance test known in the art wherein optimal performance requires mental alertness. Preferably, the subject is well rested and free from illness at the time of such testing. A brain wave pattern associated with a non-alert state of consciousness is any brain pattern that is not associated with an alert mental state. As will be appreciated by those in the art, objective performance will be monitored over time, and as performance declines, brain patterns associated therewith will be recorded and used to establish the pattern indicative of a non-alert mental state.

Because brain wave patterns associated with an alert state of consciousness may vary from subject to subject, or vary even in the same subject over time, it is preferred that the point determined to be that of the transition from an alert mental state to one of a non-alert state be such that at least about 50%, preferably at least about 75%, and more preferably, at least about 95% of the time such transition has in fact occurred. Typically, this is confirmed by the simultaneous or immediately subsequent (i.e., less than about 30 seconds, preferably less than about 10, 5, 3, 2, 1, 0.5, or 0.1 seconds) occurrence of a physical manifestation associated with a non-alert mental state, although an objective decline in performance of a task requiring an alert mental state can also be used.

In practicing this invention, it is important to monitor and analyze brain waves and/or brain wave patterns. Any monitor capable of measuring brain wave activity can be used. Examples of such monitors include EEGs.

Brain waves which are preferably monitored in accordance with this invention include alpha, beta, theta, and delta waves. Of these, several correspond to different levels of sleep, such as alpha (exhibiting brain wave activity in the range of about 8 Hz to about 12 Hz, as monitored by EEG), theta (about 6 Hz to about 8 Hz, as monitored by EEG), and delta (about 1 Hz to about 4 Hz, as monitored by EEG). Brain waves exhibiting EEG-monitored frequencies from about 12 Hz to about 30 Hz, referred to as beta waves, are characteristic of an alert state of consciousness in an individual, though beta activity at even higher frequencies has been observed in different types of mental activities. Another brain wave, referred to as a gamma wave, may also be used in the practice of this invention. As used herein, gamma activity is characterized as all EEG-monitored brain activity above about 30 Hz. As those in the art will appreciate, the boundaries between gamma and beta, beta and alpha, alpha and theta, and theta and delta are somewhat arbitrary. Thus, the foregoing delineations are intended to be exemplary and not limiting. Furthermore, use of other brain wave types or classifications useful in distinguishing an alert mental state from a non-alert mental state, whether now known or later discovered, are within the scope of the invention.

Of particular importance in the practice of the preferred embodiment of this invention is the determination of the ratio between alpha and beta brain waves detected over a particular time period, although ratios involving other brain wave forms can also be used in the practice of this invention, so long as one such form correlates with alert mental function and another correlates with non-alertness. As a subject becomes less alert, the level of alpha activity increases and the level of beta activity decreases, thus altering the alpha:beta ratio. When this ratio reaches a predetermined value (the "transition ratio"), i.e., that which has been determined to exist when the transition from an alert mental state to a non-alert state occurs, a physical stimulus is provided to restore an alert mental state. It is understood that as used herein, for convenience an "alpha" brain wave shall be considered any level of brain activity associated with a non-alert mental state, and thus in addition to brain waves having frequencies of about 8 Hz to about 12 Hz (as monitored by EEG), also includes theta, delta, and other brain waves having frequencies below those of beta waves. Similarly, for convenience, brain activity, including brain waves, associated with an alert state of consciousness are referred to herein as "beta" waves, and thus include waves having EEG-monitored frequencies from about 12 Hz to about 30 Hz and above.

The alpha:beta ratio may be expressed in terms of alpha to beta ("alpha:beta"), or beta to alpha ("beta:alpha"), which ratio is preferably calculated over consecutive periods ranging from less than about one second, from about 1 to about 5 seconds, from about 5 to about 10 seconds, and from about 10 to about 30 seconds or more. As those in the art will appreciate, because a microprocessor-based device according to the invention will enable alpha:beta ratios to be determined over almost any interval, the foregoing discussion of intervals is merely advisory, and the selection of a particular interval is left to the skilled artisan.

As those in the art will appreciate, alpha:beta transition ratios can be determined in various ways, and can be generic (i.e., as a preset value programmed into a device according hereto based upon analysis of one or more subjects other than the subject wearing the device) or individualized (i.e., determined specifically for an individual user). One way in which the alpha:beta transition ratio can be determined is to monitor (preferably continuously) alpha and beta wave activity in one or more well rested subjects during an activity requiring a high level of consciousness, e.g., reading, interactive games, etc., until such time as one or more manifestations, including physical manifestations (e.g., eyelid, jaw, and/or head movement), of a non-alert mental state are detected. In such instances, the alpha:beta transition ratio is that which is calculated to exist at the time the first manifestation(s) of a non-alert mental state is(are) detected. Alternatively, the alpha:beta transition ratio may be determined by calculating the ratio at some time prior to the occurrence of any such physical manifestation(s)(the "pre-transition period"). Preferred pre-transition periods are those from about 0.001 seconds to about 100 seconds before any physical manifestation of a non-alert mental state occur or is detectable. Of course, pre-transition periods of shorter or longer duration can also be used. In preferred embodiments of the invention, the alpha:beta transition ratio is a value calculated to occur prior to any physical manifestation of a non-alert mental state. The actual length of the pre-transition period desired is best left to the skilled artisan depending upon the particular application.

Numerous devices are currently available to detect brain wave patterns, including electroencephalographs and magnetoencephalographs. These and similar devices typically employ one or more brain wave sensors, preferably electrodes, placed in physical contact with a portion of a subject's scalp in order to detect brain wave impulses. As those in the art will appreciate, any brain wave sensor capable of monitoring or detecting brain waves can be adapted for use in the practice of this invention. Usually, the monitoring sensors attached to a patient are operably connected via cables or wires (e.g., leads) to a distal physiological monitoring instrument, which may or may not itself include a computer. One example of such a physiological monitoring instrument is the I-330 DSP-12 system (J & J Engineering, Inc., Poulsbo Wash.).

Figure 2:
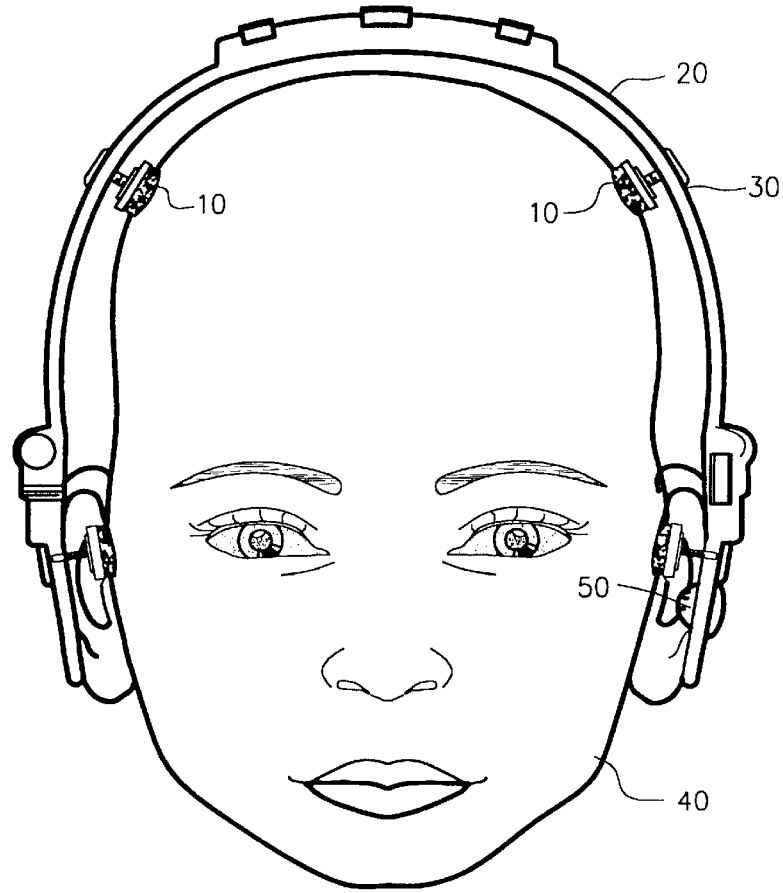
FIG. 2 is an illustration of a subject wearing a self-contained device according to the invention. Specifically, the device shown comprises two electrodes (10) for detecting brain wave activity. The electrodes contact the user's scalp in a manner such that sufficient conductive contact is made between the electrodes and the scalp so as to enable brain wave activity to be detected. The distance each electrode is spaced from the headset (20) can be adjusted by turning the threaded shaft (30) to which the electrode is attached. Of course, other ways of adjusting such spacing can be used, e.g., spring-loaded electrodes. The head set (20) illustrated incorporates, but does not a show, a processor, software, alarm component, circuitry, and power supply necessary to monitor and detect different states of mental alertness in the user (40). When a non-alert mental state is detected, the processor activates the alarm component, and an auditory stimulus is emitted from the speaker (50).

Any portion of the patient's body from which brain waves can be detected can be used as a contact area for a brain wave sensor. In preferred embodiments of the invention, the device will employ at least two sensing electrodes, each of which makes contact with the skin of subject's head, preferably with the subject's scalp. For convenience, the electrodes (or other brain wave sensor(s)) are connected to, and preferably carried in, a hat, headband, eyeglass frame, or other piece of headgear which can be comfortably worn on a user's head for extended periods. Preferred areas for electrode placement are depicted in FIG. 2. When two or more brain wave sensors are employed in a device according to the invention, it is preferred that the sensors be positioned such that when a sensor is positioned to contact a particular portion of the scalp on one side of the subject's head (see FIG. 2), another sensor is positioned to contact a substantially corresponding region on the other side of the subject's head.

Brain wave data from the brain wave sensor(s) is transmitted to the components) which then digitizes, if necessary, and analyzes the data, and, if necessary, provides notification or an alarm (or other stimulus) to the subject (typically through a perceptible physical stimulus) that a non-alert mental state exists or is imminent.

In preferred embodiments of the invention, the data gathered by the brain wave sensor(s) is transmitted to a digital processor housed in the same unit which carries the electrode. However, the processor may be located more remotely, and data can be transmitted thereto by conventional means, for instance, by an appropriate cable or wire loom. In addition, the invention envisions transmission of brain wave data to a remote processor via radio, radiotelephone, or other wireless transmission or other similar means for sending and receiving telemetry. In the event telemetry is employed, the data transmitter can be proximate or distal to the brain wave sensors. If distally located, again the transmitter would be connected to the sensor(s) via a cable or similar means. Data may be transmitted in either analog or digital form.

Upon receipt of the brain wave data from the sensor(s), it is then analyzed by a processor, preferably a small digital computer or microprocessor. If the data from the brain wave sensors is transmitted to the processor in analog form, it will first be converted to a digital form prior to processing. In preferred embodiments of the invention, prior to or as part of the processing function, the brain wave data is filtered to remove information not required for determining whether an alert or non-alert mental state exists in the subject whose brain waves are being monitored. Filters which remove brain waves of particular frequencies are known in the art, and one or more such filters can be employed. In addition, it may be desirable to filter out "noise" or other non-brain wave data included in that which is transmitted from the sensors. Methods and components for accomplishing such filtering are known in the art. For example, see U.S. Pat. No. 5,626,145.

The processor will typically then separate the brain wave data into data sets representing the various brain waves to be analyzed. For example, if only alpha and beta waves are to be analyzed, this information will be discerned from the incoming data, unless, of course, brain wave sensors specific for only a specific type of brain wave are employed, or the sensor data is preprocessed or filtered prior to its arrival at the processor, making the foregoing unnecessary. After producing the desired data sets, it is analyzed to determine if the data is indicative of an alert mental state. If so, nothing more need be done with such data, although, if desired, it may be saved to an associated storage device. Data so stored may be used for different purposes, such as to analyze when the transition from an alert to a non-alert mental state occurred. Such information would be useful in analyzing the causes of accidents, the effectiveness of the teaching regimen being employed (as it relates to keeping observers mentally alert), etc.

If, on the other hand, the data indicate that a non-alert mental state exists or is imminent, the processor activates an alarm or other notification system operably connected thereto (or otherwise associated therewith in an operable fashion) to inform the subject of the existing or imminent non-alert mental state in order to restore an alert mental state.

In preferred embodiments of the invention, the alarm is a perceptible physical stimulus, for example, a sound (or series thereof), light, pressure, vibration, shock or other electrical stimulus, or a combination of two or more different stimuli. Particularly preferred are auditory alarms based on sound. The sound may be a single frequency or multiple frequencies, and provided in simultaneous or consecutive fashion, and is preferably emitted by one or more speakers or other sound generators positioned in or adjacent to one or both ear canals of the subject. The alarm stimulus may be continuously or intermittently administered until an alert state of consciousness is restored, as monitored by the device. The amplitude or intensity of the alarm stimulus preferably should be sufficient to produce a transition from a non-alert to an alert mental state as rapidly as possible but without startling or upsetting the subject, which intensity may progressively increase until the desired mental state is restored. In particularly preferred embodiments, a device according hereto will contain a menu of alarm stimuli from which a particular subject can choose. Alternatively, in other embodiments the device is configured so that the user can select the stimuli to be employed, if necessary to restore an alert mental state.

In addition to the foregoing, the device may contain data transmission, reception, and/or other telemetry capability, such that the mental state of the subject wearing the device can be remotely monitored.

In preferred embodiments, the device according to the invention is one which, in addition to being capable of monitoring and restoring an alert mental state, can also "learn" or adapt to what constitutes a transition from an alert mental state to a non-alert mental state in a user of the device. As such, the device can be used at different times by multiple subjects, while at the same time being "customized" to the brain wave patterns of a particular user. To accomplish this, the device incorporates the software necessary to assess brain wave(s), patterns, and/or ratios associated with alert and non-alert mental states in a given subject. Of course, this capability could alternatively, or additionally, be included in a compatible device that downloads or otherwise transfers such information to a device according to the invention. Making this assessment enables the device to establish the transition ratio which, when reached, results in the alarm being activated.

A device according to the invention that is capable of "learning" preferably also contains, or is associated with a storage device that contains, a library of brain wave patterns and/or transition ratios stored in memory. Such a library may be specific to a given subject, or include information from multiple subjects. In this way, it is unnecessary for the device to "relearn" what constitutes a brain wave pattern or transition ratio for a given subject. Of course such information could be stored in a storage system incorporated into the device or be downloaded into the device, as circumstances dictate.

In order for the devices according to the invention to function, a supply of electricity is required. The particular specifications of the electric power supply employed will depend on the power requirements of the particular device, and thus this selection is left to the artisan. However, power supplies useful in the practice of this invention will include those that can be incorporated into the device, and are preferably portable and removable or detachable. Preferred power supplies include batteries and solar cells, although in many applications, it is acceptable to draw power from an external source, e.g., the electrical system of a truck or other form of transportation.

As is apparent from the above, devices such as those disclosed herein can be used to monitor whether or not an alert mental state exists in a subject wearing such a device, and if not, to restore the desired mental state, i.e., an alert state of consciousness, through stimulation of the subject by an appropriate stimulus. The devices and methods disclosed herein will find application in many fields, for example, in the transportation industry (e.g., automobile and truck drivers, pilots (of aircraft and watercraft), air traffic controllers, military personnel, and train engineers. In addition, these devices and methods will find use in any application where maintenance of an alert mental state is important, for example, amongst judges and jurors in the civil and criminal justice systems, students observing lectures, and pursuits involving hazardous activities or dangerous machinery. Devices such as those disclosed herein which contain data logging or telemetry capability will also be useful in many fields, for example, in the development of teaching techniques which promote prolonged periods of alertness. In such circumstances, it may be desirable to use a device according to the invention that partially or completely lacks the capability, whether by design or deactivation, to provide restorative stimuli in response to a detected non-alert mental state.

As those in the art will appreciate, the foregoing description is merely illustrative of preferred embodiments of the invention, and is not limiting in any way. Moreover, upon reading the foregoing, many alternative embodiments of the invention will become apparent to those skilled in the art, each of which shall be considered within the scope hereof.

Each of the documents discussed herein is hereby incorporated by reference in its entirety, and any such discussion shall not constitute an admission as to whether or not any such reference is prior art.

I claim:

1. A device for maintaining a state of mental alertness, the device comprising:
   (a) a brain wave sensor;
   (b) a processor that receives data from the brain wave sensor, which processor analyses brain wave types detected by the brain wave sensor to determine if a subject using the device is in an alert mental state, wherein the analysis of brain wave types is a determination of a ratio between at least two different brain wave types to detect a non-alert mental state;
   (c) a component or delivering a stimulus to the subject, wherein the component can be activated by the processor to deliver the stimulus if the processor determines that the subject has a non-alert mental state; and
   (d) a power supply for the brain wave sensor, processor, and component.

2. A device according to claim 1 comprising more than one brain wave sensor.

3. A device according to claim 1 wherein the brain waive sensor comprises an electrode which makes contact with skin of the user's head.

4. A device according to claim 1 wherein the device is capable of being worn by the user.

5. A device according to claim 1 wherein the determined ratio is input into the processor and analyzed by comparing the determined ratio against a library of brain wave type ratios stored in a memory operably connected to the processor in order to determine if the determined ratio input into the processor is indicative of a non-alert mental state.

6. A device according to claim 5 wherein the library of brain wave type ratios has been derived previously from the user while in an alert state of consciousness.

7. A device according to claim 5 wherein the processor analyses the determined ratio at least once every fifteen seconds.

8. A device according to claim 5 wherein the processor analyses the determined ratio at least once per second.

9. A device according to claim 1 capable of detecting a brain wave type selected from the group consisting of an alpha, beta, theta, and delta brain wave, and any combination of two or more of the foregoing brain wave types.

10. A device according to claim 1 wherein the determined ratio comprises an alpha:beta ratio.

11. A device according to claim 1 wherein the component emits a stimulus perceptible to the user that is sufficient to transition the user from a non-alert mental state to an alert mental state.

12. A device according to claim 11 wherein the stimulus emitted from the component is selected from the group consisting of an auditory stimulus, a visual stimulus, an electrical stimulus, a vibratory stimulus, and a combination of more than one of the foregoing stimuli.

13. A device according to claim 11 wherein the component comprises an alarm positioned in or adjacent to an ear canal of the user in a manner such that an auditory stimulus emitted by the alarm can be perceived by the user in order to restore an alert mental state.

14. A device according to claim 13 wherein the auditory stimulus emitted by the component can be selected by the user.

15. A device according to claim 1 wherein the power supply comprises of at least one battery.

16. A device according to claim 1 wherein the brain wave sensor is integrated into an article to be worn by the subject.

17. A device according to claim 1 wherein the brain wave sensor and component are integrated into a single removable apparatus to be worn on the user's head.

18. A device according to claim 1 wherein the brain wave sensor, processor, and component are integrated into a single removable apparatus to be worn on the user's head.

19. A device according to claim 18 further comprising a power supply integrated therein.

20. A method for monitoring a state of consciousness in a subject, the method comprising:

(a) detecting at least two brain wave types in the subject and calculating a ratio between two of those brain wave types; and (b) comparing the calculated ratio between brain wave types with a ratio indicative of an alert sate of consciousness.

21. A method for maintaining an alert state of consciousness in a subject, the method comprising:

(a) detecting at least two brain wave types in the subject and calculating a ratio between two of those brain wave types; and (b) determining if the calculated ratio is indicative of an alert mental state of consciousness, and if not, stimulating the subject until a calculated ratio between at least two brain wave types indicative of an alert state of consciousness is detected.

22. A method for maintaining an alert state of consciousness in a subject, the method comprising:

(a) detecting two brain wave types in the subject and calculating a ratio there between to determine if the subject is producing a brain wave type ratio indicative of a non-alert state of consciousness; and, if so (b) providing a stimulus until an alert mental state is achieved.

* * * * *